Figure 1:
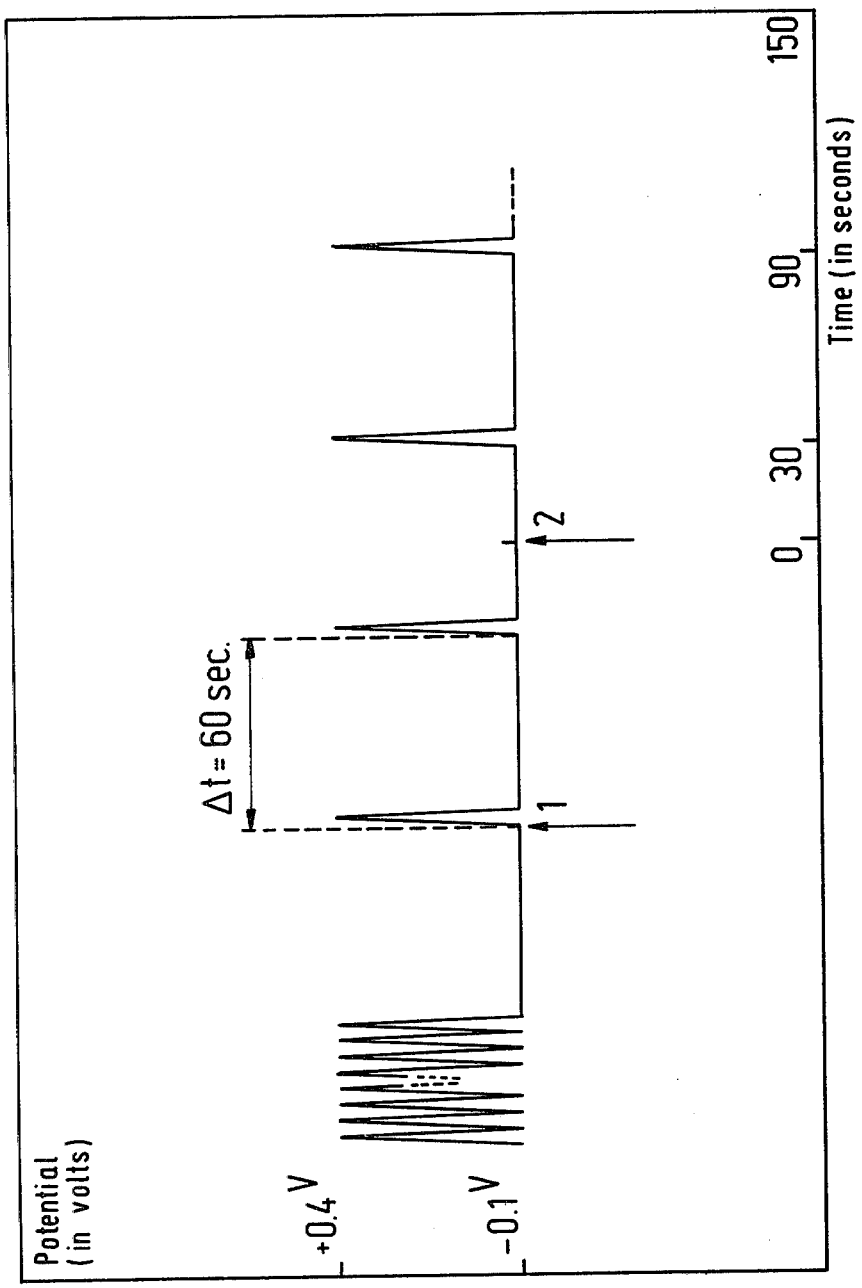

United States Patent [19]

Jozefonvicz et al.

[11] 4,304,853

[45] Dec. 8, 1981

[54] METHOD OF DETERMINATION FOR PROTEASES AND ANTIPROTEASES

[76] Inventors: Marcel Jozefonvicz; Jean M. Nigretto, both c/o Hoechst Aktiengesellschaft, D-6230 Frankfurt am Main 80, Fed. Rep. of Germany

[21] Appl. No.: 142,655

[22] Filed: Apr. 22, 1980

[30] Foreign Application Priority Data

Apr. 24, 1979 [FR] France .................. 79 10305
Dec. 17, 1979 [FR] France .................. 79 30820

[51] Int. Cl.³ .............................................. C12Q 1/56
[52] U.S. Cl. .................................. 435/13; 435/24; 435/23; 204/72
[58] Field of Search ............... 435/13, 23, 24; 204/72

[56] References Cited

U.S. PATENT DOCUMENTS

| 3,884,896 | 5/1975 | Blomback et al. ............ 435/13 |
| 3,886,136 | 5/1975 | Claeson et al. ............... 435/13 |
| 4,216,142 | 8/1980 | Ali ............................... 435/13 |
| 4,221,706 | 9/1980 | Ali et al. ...................... 435/13 |

FOREIGN PATENT DOCUMENTS 54-128191 10/1979 Japan .................. 435/13

*Primary Examiner*—Benoît Castel
*Attorney, Agent, or Firm*—Curtis, Morris & Safford

[57] ABSTRACT

A method for the determination of proteases and antiproteases, especially those of the blood clotting system and of the complement, is described, according to which a fragment liberated from a substrate by enzymatic hydrolysis is determined electrochemically.

19 Claims, 9 Drawing Figures

METHOD OF DETERMINATION FOR PROTEASES AND ANTIPROTEASES

The present invention relates to a new method of determination for proteases and antiproteases, and in particular proteases and antiproteases of the blood clotting systems and of the complement.

Data on the enzyme activity of the blood and in particular of the "trypsin-like" proteases are crucial if any anomalies in the blood clotting factors are to be recognized. This determination likewise very frequently provides extremely important data on more serious disturbances in the organism. For this reason, it is extremely important to have available a reliable and accurate method of determination for these enzymes. The methods of determination currently in use are in the main based on a photometric determination (simple photometry, spectrophotometry or fluorescence photometry) of chromogenic or fluorescent groups obtained after the splitting of specific substrates by the enzymes to be determined.

Most of the substrates used are synthetic substrates. They are outstandingly suitable for the determination of blood enzymes and also for the investigation of the reactions which cause the formation, the inhibition or the consumption of these enzymes, and even for the determination of factors which influence or participate in these diverse reactions (compare, in particular, French Pat. Nos. 2,183,188, 2,317,278, 2,317,280 and 2,293,439).

Unfortunately, these elegant methods of determination are accurate only in a homogeneous medium. In heterogeneous media, such as biological fluids (and in particular whole blood), their accuracy decreases significantly. In order to circumvent this decisive disadvantage, it has been proposed to use centrifuged blood, that is to say blood without solids, which consequently is better suited for photometric methods. Apart from the fact that this centrifuging requires appropriate equipment, which is heavy and complex, and that is constitutes a source of unavoidable losses, it also results in a certain "traumatism" of the blood, which leads to the release of non negligible amounts of diverse factors from the thrombocytes; these factors themselves possess a certain enzyme activity and consequently falsify the results of the determination.

The object of the present invention is, accordingly, to provide a new method of determination for the above-mentioned enzymes, which method is better suited to the needs of practice than are the methods of determination known hitherto, and in particular is better suited due to the fact that it is simple, accurate and reliable and that it can be used in homogeneous or heterogeneous media as well as in solutions or suspensions.

The present invention relates to a new method of determination for proteases and antiproteases, and in particular proteases and antiproteases of the blood clotting systems and of the complement, which comprises bringing together, in an aqueous medium, the enzyme and a substrate A - B, in which A denotes a peptide radical, the N-terminal (amino terminal) nitrogen atom of which is optionally substituted and the C-terminal (carboxy terminal) aminoacid of which is arginine, or N-substituted arginyl, and B denotes the radical of an amine H - B which can be oxidized or reduced electrochemically, and determining the amine which has been split off by means of amperometry.

U.S. Pat. No. 3,367,849 discloses a method of determination for glucose which is based on the amperometric determination of ferricyanide ions.

If this electrochemical determination is to proceed satisfactorily, the specific substrate of the corresponding enzyme must not be electrochemically oxidized or reduced under the conditions of the determination, conducting or semi-conducting electrodes must be used and, in addition, the product resulting from hydrolysis of the substrate by the enzyme must itself be electroactive and the current strength measured must be directly proportional to the amount of enzymes in the particular medium.

According to an advantageous embodiment of the method of determination according to the invention, the increase in the concentration of the electroactive compound, which is the product resulting from hydrolysis of the substrate, is monitored periodically in the measurement cell with the aid of the change in the oxidation or reduction current.

According to the specific embodiment, the said oxidation or reduction current is obtained from the height of the peak in the current-voltage characteristic which results when an alternating voltage is applied.

The height of the current-voltage peak is in fact proportional to the concentration of the electroactive product of the enzymatic hydrolysis, which is present in the solution and on the surface of the measurement electrode.

According to an advantageous embodiment of the method of determination according to the invention, the measurement electrode is pre-conditioned before the actual determination by applying a saw-tooth potential, the amplitude of which varies between $-0.1$ V and $+0.4$ V and which changes at a rate of 0.2 V/second, until the measurement curve $i=f(U)$ recorded on a recorder has reached a limiting curve.

This preconditioning is necessary because the current values measured during the hydrolysis are very low. It serves to impart to the electrode a reproducible and precisely defined surface state before each cycle. By virtue of this preconditioning, the electrochemical measurements carried out in accordance with the present invention are particularly sensitive and reliable.

According to an advantageous embodiment of the method according to the invention, the measurement electrode is an electrode made of a noble metal, such as platinum, gold or silver, or special steel, or an electrode made of carbon paste.

According to a further advantageous embodiment, the medium in which the determination is carried out can be either aqueous or non-aqueous and the determination can be carried out over the entire pH range.

It is possible to carry out the determination kinetically or as an end point method.

In a preferred embodiment of the method, the substrate consists of an oligopeptide to which an aromatic or heterocyclic amine or polyamine is bonded. In the method according to the invention, the enzyme to be determined splits the bond between the amino acid which is at the carboxyl end and the amine or polyamine. The measurement method comprises the electrochemical determination of the amount of amine or polyamine which is liberated.

Suitable amines or polyamines are: p-aminodiphenylamine, 4,4'-benzidine or o-dianisidine.

Further amines which can be used are: p-nitroaniline and 4-methoxy-2-naphthylamine.

In a preferred embodiment, the substrate contains the following amino acid radical or peptide radical: benzoyl-arginyl, tosyl-arginyl, tosyl-L-glycyl-L-prolyl-L-arginyl, H-D-phenylalanyl-L-pipecolyl-L-arginyl, N-benzoyl-L-phenylalanyl-L-valyl-L-arginyl or H-D-phenylalanyl-L-pipecolyl-L-arginyl.

According to a special feature of this embodiment, the substrate consists of H-D-phenylalanyl-L-pipecolyl-L-arginyl-p-amino-diphenylamide dihydrochloride (H-D-Phe-Pip-Arg-pADA, 2 HCl) and the enzymatic reaction takes place in accordance with the reaction equation given below: H-D-Phe-Pip-Arg-pADA, 2HCl + Thrombin → H-D-Phe-Pip-Arg-OH + pADA (as the electroactive amine product).

According to a further advantageous embodiment of the subject of the invention, and in order to prevent precipitation of the substrate, 2 to 10% of dimethylsulfoxide are added to the reaction medium.

The present invention relates in particular to the new electrochemical method of determination for proteases and antiproteases of the blood clotting systems and of the complement, and specifically of trypsin, plasmin, kallikrein, factor XII (Hageman factor), factor XI (plasma thromboplastin antecedent), factor X (Stuart-Prower factor), factor IX (Christmas factor), enzymes $C_1$ and $C_3$ of the complement system, and the antiproteases, such as antithrombin III, $C_1$-inactivator, alpha$_2$-macroglobulin, antiplasmin, alpha$_2$-antitrypsin and the like, and also to the agents and procedures which are suitable for carrying out this method and which make use of the method and the substrates of the present invention. The invention can be better understood with the aid of the supplementary description given below, which relates to illustrative embodiments of the electrochemical method of determination, for proteases and antiproteases, of the present invention.

However, it is pointed out that the examples given below, and also the examples of calibration curves and of kinetic curves for the hydrolysis of benzoyl-D,L-arginine-p-aminodiphenyl-amide, HCl [=D,L-BAPADA] which are shown in the drawings appertaining thereto, and also the example of a determination in a non-aqueous medium and the example of the preparation of an electrode with carbon paste are given merely by way of illustration of the subject of the invention and in no way are to be understood as constituting a limitation.

EXAMPLE

I. Equipment used (a) A potentiostat, which is intended to maintain a constant potential difference between the measurement electrode and the reference electrode. A saw-tooth function generator, which generates a potential which varies between $-0.1$ and $+0.4$ V at a rate of 0.2 V/second. A graphic recorder with a good dynamic performance. A polytetrafluoroethylene cell which has a capacity of 5 ml and can hold three electrodes.

(b) Measurement electrode: This consists of a platinum plate which is surrounded by a cylinder of polytetrafluoroethylene (surface area 0.0314 cm$^2$).

(c) Reference electrode: Calomel electrode (SCE); all voltage levels are measured with reference to this electrode.

(d) Auxiliary electrode: This serves to ensure the passage of the current. It consists merely of a durable metallically conducting wire (platinum).

(e) Solutions: The stock solutions of the enzyme (solution E) and of the substrate (solution S) are freshly prepared. The test solution, to which a given amount of E is added at the time $t=0$ of the kinetics, is termed A. The buffer, which has a pH of 8.15, is made up of 0.025 M Veronal$^{(R)}$ and NaCl with an ionic strength of $F=0.15$.

(f) Example of an electrode made of carbon paste: 15 g of pure carbon powder are mixed with 9 ml of paraffin oil, for example that sold commercially under the trade name Nujol$^{(R)}$. An electrode with a surface area of 0.16 cm$^2$ and a thickness of 3 mm can be shaped from the homogeneously mixed paste.

Figure 8:
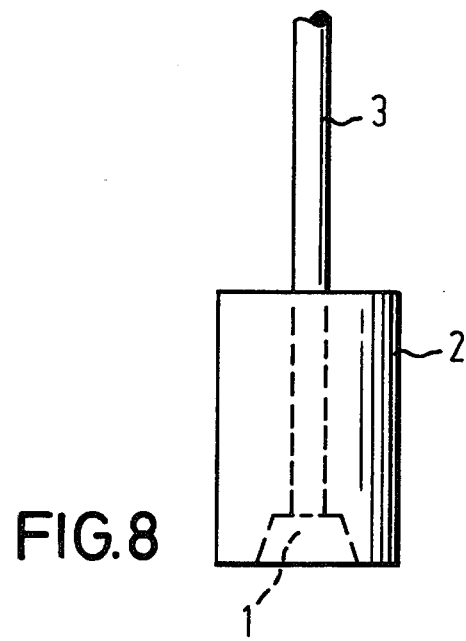
Figure 9:
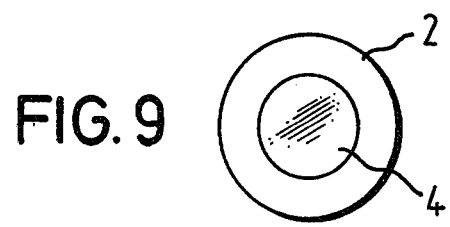

FIGS. 8 and 9 of the appended drawings show an electrode of this type and in particular show a front view (FIG. 8) and a view from below (FIG. 9).

The paste, which has been homogenized well, is pressed into the cavity 1 of a cylinder 2, which, for example (but not necessarily), is made of polytetrafluoroethylene. This cylinder 2 has a hollow center, so that a fine cylindrical carbon rod 3 can be introduced, this rod connecting the surface of the electrode 4 with the electrical circuit (not shown on the drawing). It is essential that the surface 4 is renewed before each determination.

II. Preconditioning of the electrode

The measurement electrode is preconditioned in solution A without the enzyme, in order to impart to it a reproducible and precisely defined surface state before each cycle.

The preconditioning is achieved by applying a potential which has a saw-tooth profile and changes as a function of time, the potential varying between $-0.1$ and $+0.4$ V and changing at a rate of 0.2 V/second.

The conditioning is complete when the signal $i=f(U)$ on the recorder has reached a limiting curve after about two minutes.

The electrode can then be used for the kinetic determinations, for which purpose the same saw-tooth potential as for the conditioning is applied every 60 seconds.

III. Recording of the base current

After conditioning, the first two cycles recorded (at an internval of 60 seconds) show the profile of the base current, the values of which must be deducted from the current levels which are measured during the hydrolysis.

FIG. 1 shows the way in which the saw-tooth voltage applied changes with time, this voltage being applied before and after the addition of the enzyme solution (2). A single saw-tooth pulse is triggered every 60 seconds. The typical base current (1) is recorded during a further pulse.

When a base current (1) which is reproducible to an accuracy of 0.01 microamperes has been obtained, the enzyme is added at the time $t=0$ of the triggering of a further pulse.

This signal is not recorded. Recording of the subsequent signals enables the progress in the hydrolysis of the substrate by the enzyme to be recorded every 60 seconds.

IV. Graphical evaluation of the results

After deducting the base current at the particular potential, the current levels recorded at the maximum value of any one wave $i=f(U)$ are proportional to the concentration of the electroactive species liberated during the hydrolysis. In the case of short hydrolysis times, a plot of the current levels against time is linear. The relationship between the enzyme concentration E (in μg/ml) and the rate of hydrolysis at time 0 (represented by the ratio $(di/dt)_o$ in μA/minute, that is to say by the gradient of the curve $i=f(t)$ at the origin) for an electrode with a surface area of 1 cm² is given by the following formula:

$$E = K(di/dt)_o$$

Figure 2:
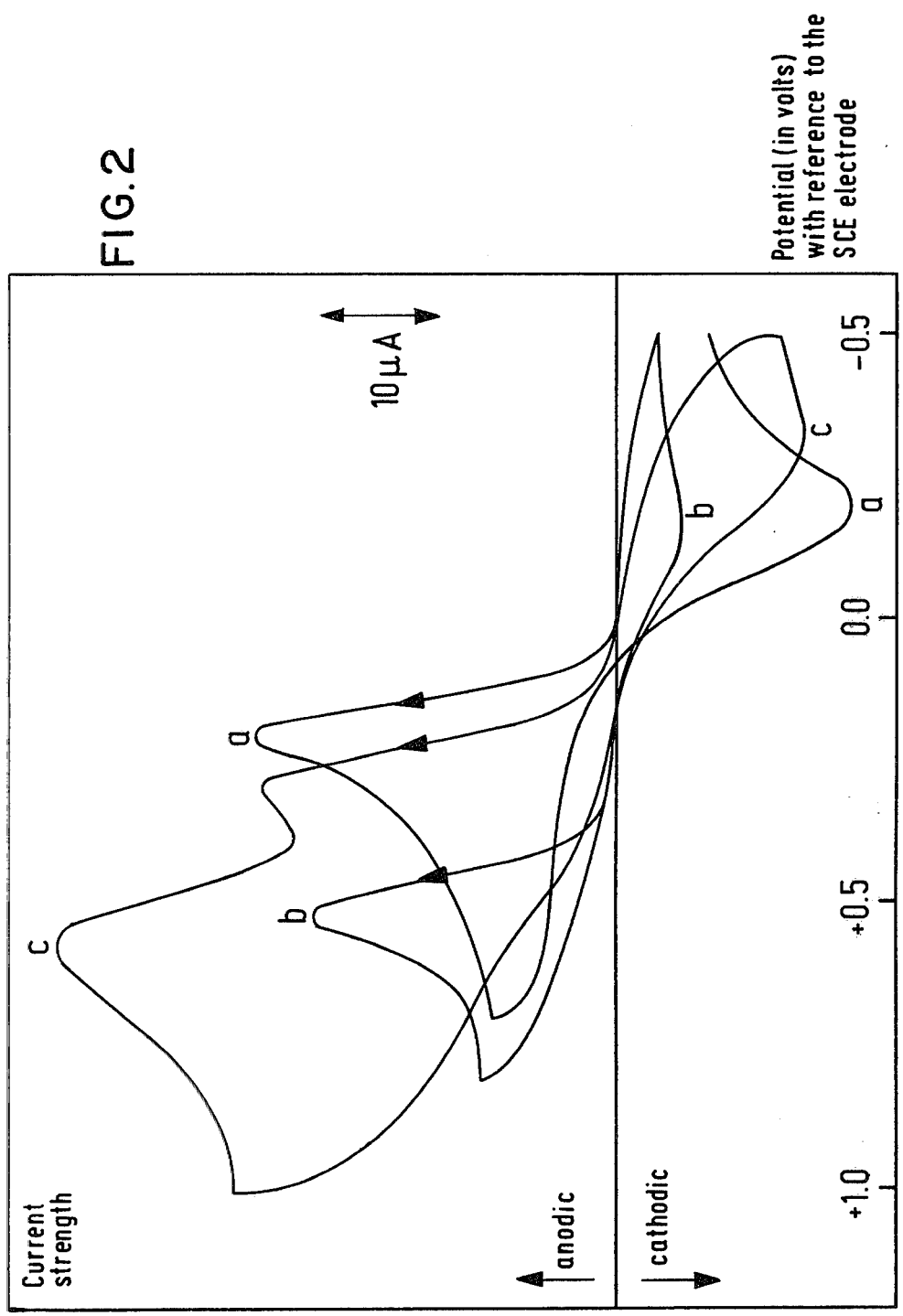

The coefficient K depends on the nature of the enzyme and of the substrate which are used. cl V. Recording of the cyclic voltage/current curves of pADA with a carbon paste electrode FIG. 2 shows the voltage/current curves obtained at pH 8.15 and at a scanning speed of 0.2 V/second. The electrode is a carbon paste electrode. The oxidation peak value of pADA—0.22 mM—(curve a) is the result of the transfer of two electrons into a region of potential where the base current is not influenced by the oxygen reduction.

Curve B, shown in FIG. 2, shows the electroactive behavior of the substrate in the region of anodic potential values, and specifically in this case of D,L-BAPADA in a concentration of v1/mM. As can clearly be seen from FIG. 2, the maximum assigned to BAPADA, at about −0.3, has been displaced with respect to the oxidation peak of pADA. This is probably due to the benzoyl-arginyl group. On the other hand, the fact that the oxidation peak in the case of the substrate is considerably lower can be explained by the fact that the diffusion coefficient of the substrate is approximately 40 times smaller than that of the liberated amine. Curve c shows the current/voltage characteristic which results when the substrate (D,L-BAPADA, 1/mM) and the hydrolysis product (pADA 0.22 mM) are present together; notwithstanding the anodic shift of the peak in the case of pADA, the voltage/current curves a and b resemble curve c in respect of the current levels. This amperometric procedure shows that the linear relationship between the maximum amplitude and the concentration of the amine (pADA) is the result of an adequate separation of the anodic current maxima.

Figure 3:
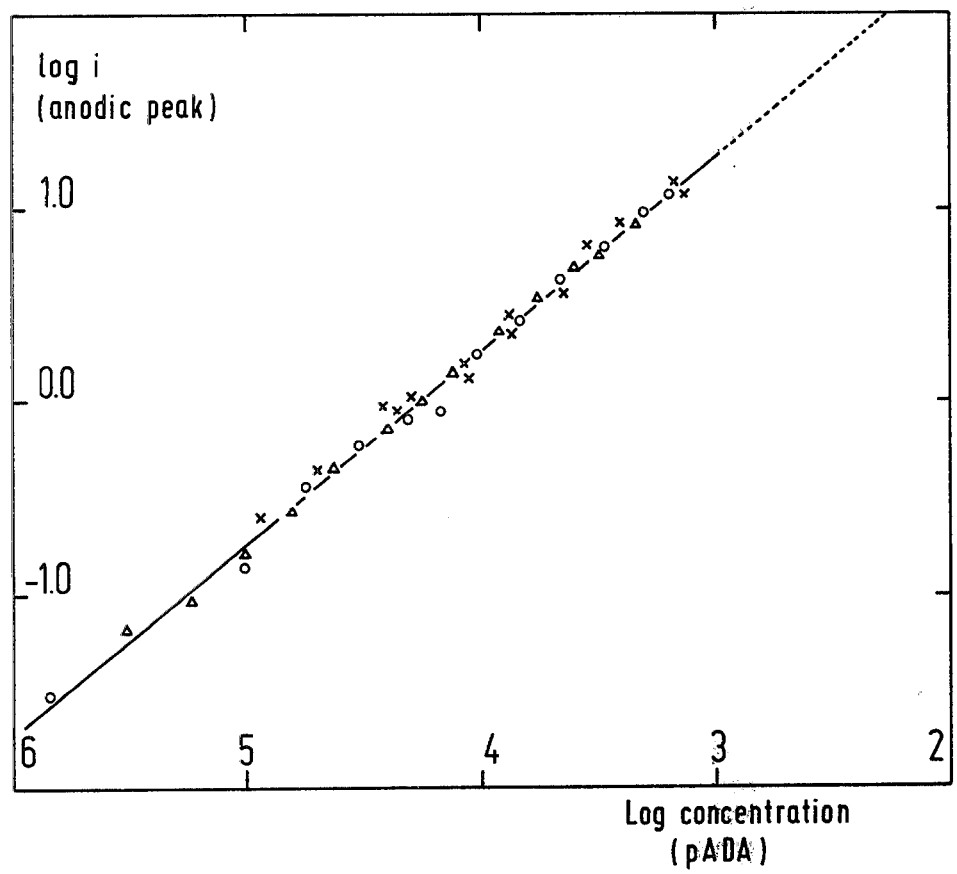

VI. Recording of the amplitude of the anodic maxima as a function of the pADA concentration at a platinum electrode FIG. 3 shows the voltametric calibration curve and the anodic current maxima (as the ordinate) as a function of the pADA concentration.

The measurement points shown as X are those for pADA on its own, the measurement points o are those for pADA in the presence of 1 mM of D,L-BAPADA and the points Δ are those for pADA in the presence of 75 μg/ml of trypsin.

The conditions were as follows:

| Temperature: | 30° C. |
| pH = | 8.15 (TRIS buffer) |
| Amount of DMSO added: | 6.35% |
| Scanning speed: | 0.2 V/second |
| Polished platinum electrode | |

As can be seen from FIG. 3, the plot is a perfect straight line. The profile of the voltage/current curve of pADA changes slightly only when the amount of trypsin is above 100 μg/ml, but no charge transfer is observed in the case of the triangular function located between −0.1 and +0.4 V (Calomel electrode ECS) at the scanning speed of about 0.2 V/second.

Although the addition of the blood clotting factors of the blood, such as fibrinogen, prothrombin or thrombin results in their adsorption on the platinum electrode (compare, in particular, L. DUIC et al., J. Electrochem. Soc. 120 (1973), pages 348–361) and although, in the case of these enzymes, charge transfer processes take place which result in the appearance of two maxima (one anodic and one cathodic), the position of these maxima can be located only after cyclic scanning at 0.05 V/second for at least 10 minutes, which is never the case under the conditions of the present invention, particularly since the conditions required in the present invention, such as the presence of the buffer (pH 8.15) and the preconditioning of the electrode, make the appearance of these two maxima virtually impossible.

VII. Measurement of the enzyme activity of trypsin

Figure 4:
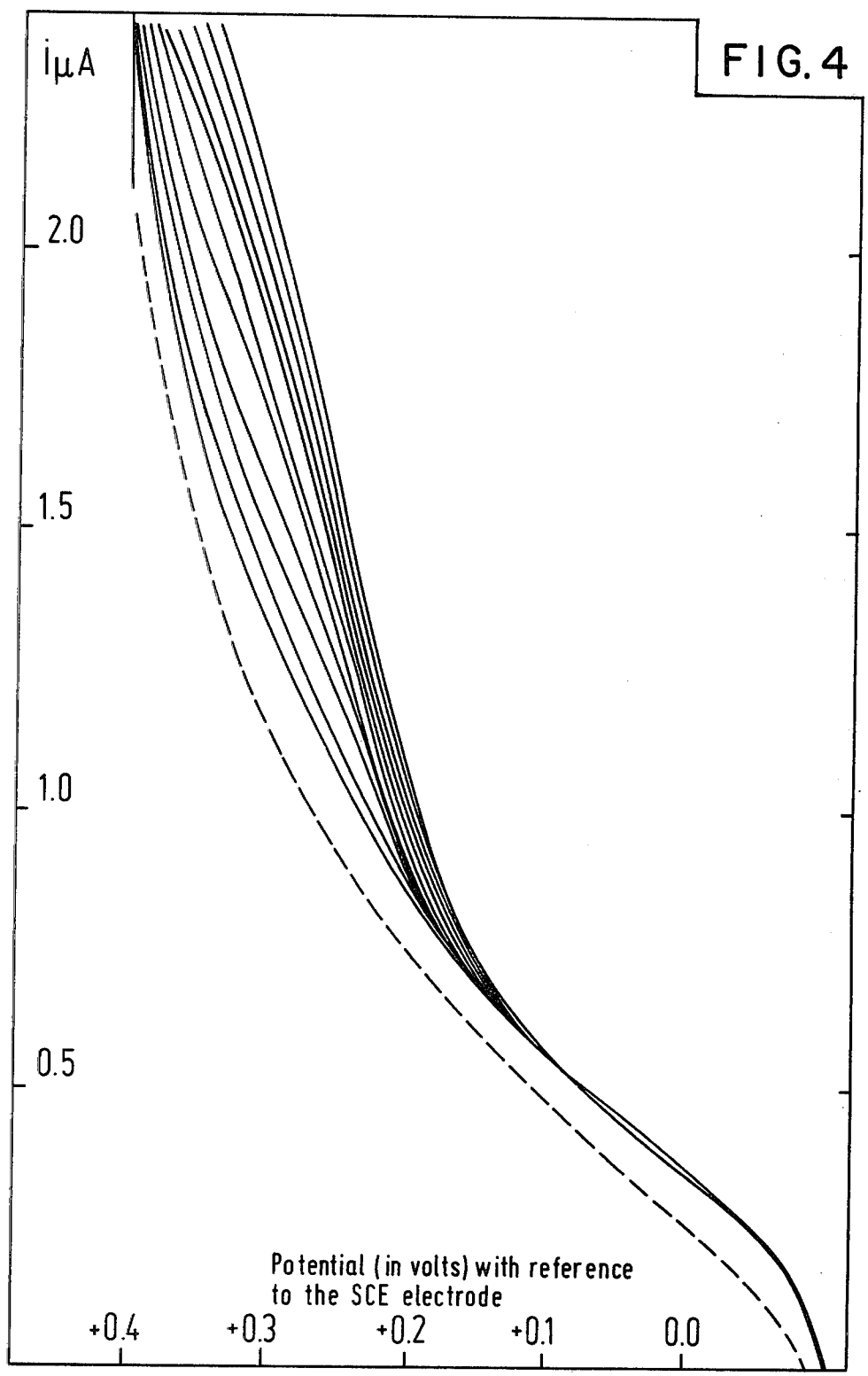

FIG. 4 shows the voltage/current curves for the oxidation of pADA recorded during the hydrolysis of D,L-BAPADA wth trypsin.

| Conditions: | |
| --- | --- |
| Temperature: | 30° C. |
| pH = | 8.15 (TRIS buffer) |
| DMSO: | 6.35% |
| Polished platinum electrode | |
| Scanning speed: | 0.2 V/second. |

Figure 5:
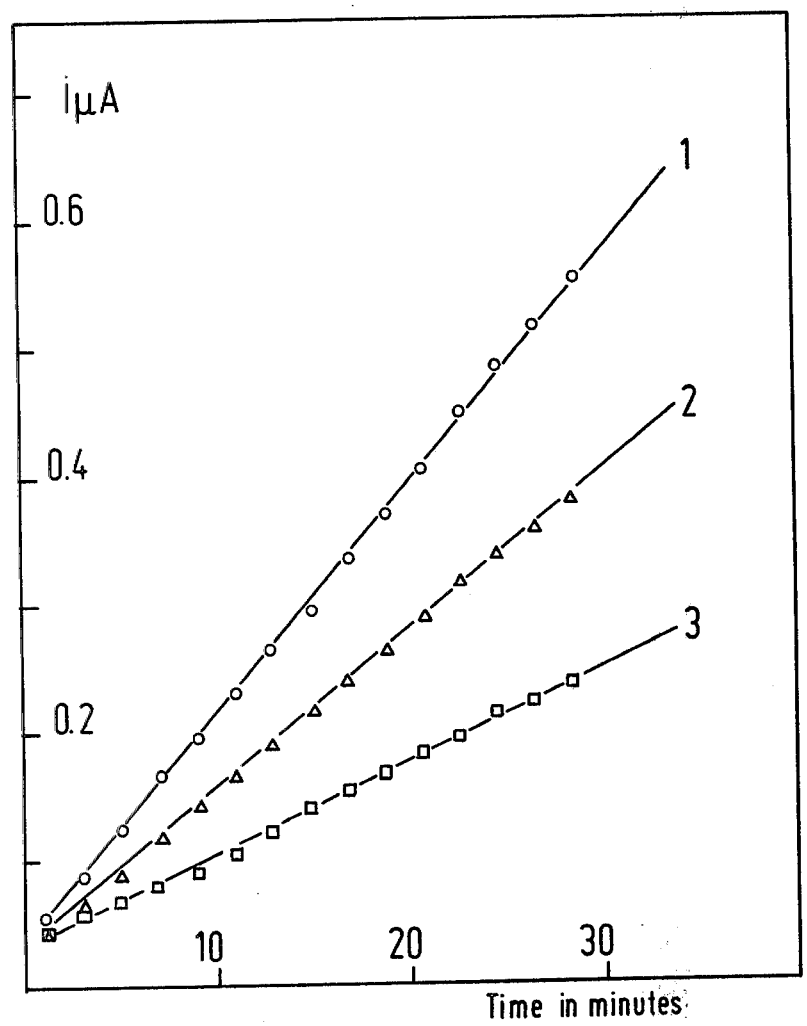
Figure 6:
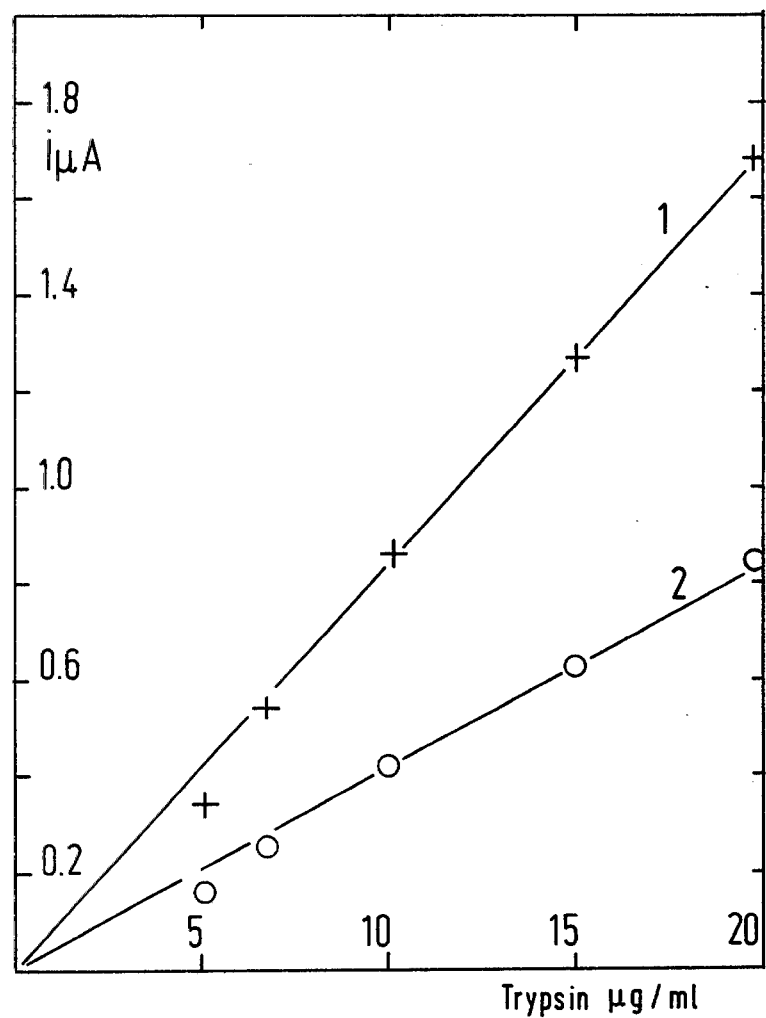

The enzyme solution is added at the end of the potentiodynamic cycle which serves to record the base current (the base current has been shifted downwards; it is represented by the broken line). The concentrations corresponding to the current maxima can be read off from the calibration curve (FIG. 3). The conversion is determined as a function of time (maximum 30 minutes). FIG. 5 shows the hydrolysis of D,L-BAPADA with 5.5 μg/ml (curve 1), 8.3 μg/ml (curve 2) and 11.0 μg/ml (curve 3) of trypsin as a function of time. The conditions are the same as those which have been described for the recording of the maximum anodic current levels. FIG. 6 shows the conversion as a function of the concentration of the enzyme (curve 1 after 5 minutes hydrolysis and curve 2 after 10 minutes hydrolysis). It is a first order reaction. The classical constants such as Km and Vm are determined by the conventional method from a LINEWEAVER-BURK diagram, which shows the specific rate of reaction as a function of the concentration of the substrate.

Figure 7:
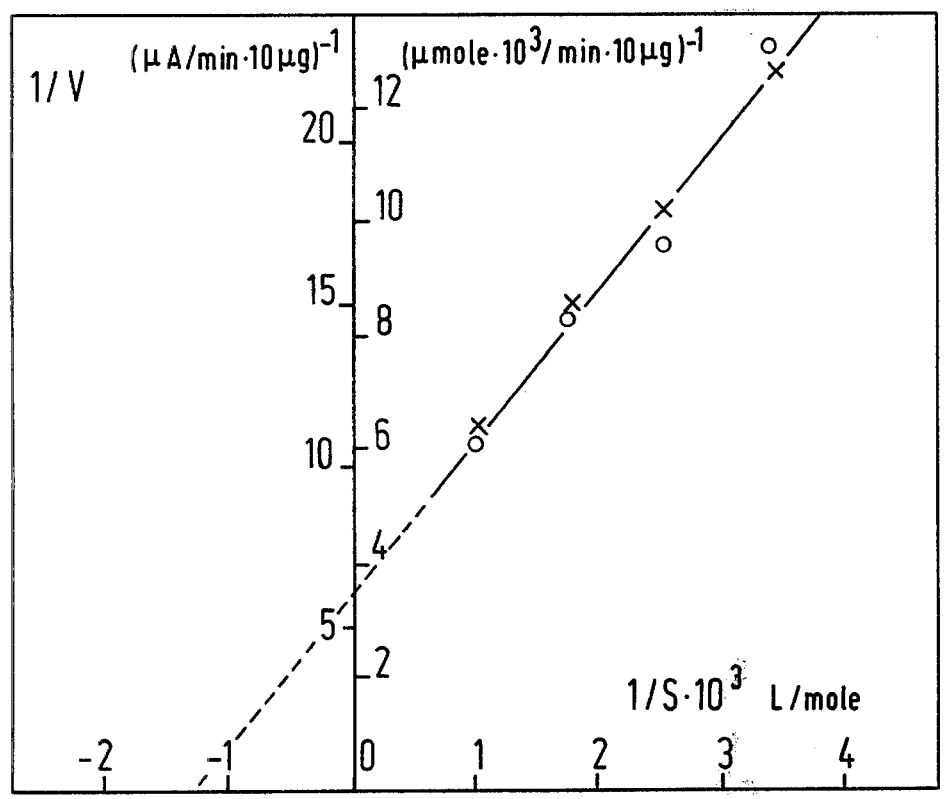

FIG. 7 shows such a LINEWEAVER-BURK diagram for the hydrolysis of D,L-BAPADA with trypsin (10 μg/ml). The reciprocal value of the rate (1/V) has been plotted as the ordinate and the reciprocal value of the concentration of the substrate (1/S) has been plotted as the abscissa. The reciprocal value of the rate 1/V was expressed as follows: either as (μA/minute—10 μg of enzyme)$^{-1}$ or as (μ mol × 10³ of pADA/minute—10 μg of enzyme). The points o represent an average value of 10 measured values for the rate and the points X represent a graphical average value. Each point was obtained using a fresh enzyme stock solution.

| Experimental conditions: | |
| --- | --- |
| Trypsin concentration: | 10 μg/ml |
| Temperature: | 30° C. |
| pH = | 8.15 (TRIS) |

| -continued |  |
|---|---|
| Experimental conditions: | |
| DMSO: | 6.35% |

The MICHAELIS-MENTEN constant Km and the maximum rate Vm, which can be obtained from the LINEWEAVER-BURK diagram shown in FIG. 7, are $8 \times 10^{-4}$ moles/liter and $9.6 \cdot 10^{-10}$ moles/minute.μg.

VIII. Measurement of the enzyme activity of thrombin

The procedure is similar to that for trypsin and is also suitable for the determination of further enzymes, also with the aid of other substrates. The data are summarised in Table 1. For thrombin, the kinetic data are: $Km = 10^{-5}$ moles/liter and $Vm = 1.1 \times 10^{-7}$ moles/minute × I.U.

| ENZYME | TRYPSIN | THROMBIN |
|---|---|---|
| Substrate | Benzoyl-D,L-arginine-p-aminodiphenyl-amide, HCl (D,L-BAPADA) | H-D-Phenylalanyl-L-pipecolyl-L-valyl-L-arginyl-p-amino-diphenylamide, 2HCl (HDL) |
| Electroactive species liberated | p-Aminodiphenylamine (pADA) | pADA |
| Substrate solution S | 7.65 mg of D,L-BAPADA in 1 ml of DMSO | 0.40 mg in 1 ml of Veronal$^{(R)}$ buffer |
| Test solution A | 0.2 ml of solution S + 3 ml of 0.025 M Veronal$^{(R)}$ buffer of pH 8.15 + NaCl (ionic strength 0.15) | 0.4 ml of solution S + 2 ml of Veronal buffer |
| Standardization | After hydrolysis of the substrate with 1 mM of trypsin for one minute, a current of 0.295 μA/cm$^2$ of electrode surface area results | The hydrolysis of 0.1 mM of substrate with 0.01 I.U. of thrombin for one minute gives a current of 0.217 μA/cm$^2$ |
| Results | Ratio between the enzyme concentration E (in μg/ml) and the rate of hydrolysis at time O (represented by the ratio (di/dt)o) with an electrode with a 1 cm$^2$ surface area E = 3.39 (di/dt)o E = in μg/ml (di/dt)o in μA/minute. | Ratio between the enzyme concentration E (in I.U.) and the rate of hydrolysis at time O (represented by the ratio (di/dt)o) with an electrode of 1 cm$^2$ surface area E = 0.046 (di/dt)o (dimensions: as on the left) |

IX. Antithrombin in the blood

The blood is treated with sodium citrate in the customary manner. 0.2 ml of this blood in 2.8 ml of Veronal$^{(R)}$ buffer is incubated with 4,000 I.U./liter of heparin for one minute at 40° C. 50 μl of a thrombin solution containing 60 I.U./ml are then added and the mixture is incubated for 4 minutes. 250 μl of a solution of HDL, which had been obtained by diluting 1 ml of a solution containing 0.7 mg of HDL with 2 mg of Veronal$^{(R)}$ buffer and which had been pre-incubated at 40° C., are then added with stirring. After incubating for precisely 30 seconds, the reaction is blocked by adding glacial acetic acid and the current is measured. Using the measured values for a sample T containing thrombin and buffer but no blood and for a sample P containing thrombin, buffer and blood, and assuming that the values measured for normal blood are $T_n$ and $P_n$, the activity of the antithrombin is given by the formula $$\frac{i_T - i_P}{i_{Tn} - i_{Pn}} \times 100$$

in % of antithrombin activity based on normal blood.

X. Preparation of the substrate D,L-BAPADA 4.68 g (0.0168 mole) of benzoyl-L-arginine are dissolved in a mixture of one equivalent of 85% strength orthophosphoric acid and 25 ml of diethyl phosphite and the solution is heated in an oil bath. 1 equivalent of pADA, 2 equivalents of pure triethylamine and a solution of 2 equivalents of phosphorus pentoxide in 20 ml of diethyl phosphite are added. The whole is shaken and the reaction mixture is heated, whilst stirring well and under nitrogen. It is then cooled and the crude product is separated from the mother liquor. 300 ml of 1 N HCl are then added and the mixture is warmed. It is stored overnight in a refrigerator and the upper phase is decanted off. The residual oil is extracted, and washed, with ice-cold acetone. The product is then recrystallized from an ether/ethanol mixture.

The yield is about 55%.

| Elementary analysis: (BAPADA = $C_{25}H_{29}O_2N_6Cl$) | | | | | | |
|---|---|---|---|---|---|---|
| | C | H | N | O | P | Cl |
| Calculated: | 62.5 | 6.02 | 17.5 | 6.67 | 0 | 7.38 |
| Found: | 60.9 | 6.16 | 16.6 | 8.60 | 0.2 | 7.20 |

The IR, UV and NMR spectra show that the product obtained is indeed D,L-BAPADA.

XI. Kinetic constants of trypsin and thrombin

These constants (summarized in Table II below) have been obtained with the aid of the electrode prepared in accordance with Example I f). The buffers used are the following:

TABLE II a: Tris (0.025 M), NaCl (0.12 M), glycine (0.05 M), DMSO 4.76%
Temperature: 20° C., pH = 8.3
b: Veronal® (0.025 M), NaCl (0.12 M), DMSO 6.35%
Temperature: 30° C., pH = 8.4

| ENZYME | SUBSTRATE | $V_M$ | $K_M$ |
|---|---|---|---|
| Trypsin | Benzene-D,L- | | |

TABLE II-continued a: Tris (0.025 M), NaCl (0.12 M), glycine (0.05 M), DMSO 4.76%
Temperature: 20° C., pH = 8.3
b: Veronal ® (0.025 M), NaCl (0.12 M), DMSO 6.35%
Temperature: 30° C., pH = 8.4

| ENZYME | SUBSTRATE | $V_M$ | $K_M$ |
|---|---|---|---|
| | arginine-pADA-hydrochloride | 0.00096 | $8 \times 10^{-4}$ (b) |
| Thrombin | H—D—Phe—Pip—Arg—pADA | 0.10 | $1 \times 10^{-5}$ (a) |
| | H—D—Phe—Pip—Arg—4—MBNA | 0.020 | $3.7 \times 10^{-5}$ (a) | pADA: para-aminodiphenylamide
MBNA: methoxy-$\beta$-naphthylamide
$V_M$: maximum rate expressed in $\mu$mole/minute I.U.
$K_M$: Michaelis constant in mole/1

XII. Determination of the enzyme hydrolysis product in a non-aqueous medium

The procedure corresponds to that of Example IX, except that 2 ml of chloroform were added after the hydrolysis had been blocked by acidifying with an equal volume of 50% strength acetic acid or 0.15 M hydrochloric acid. After shaking vigorously, the aqueous upper phase is removed with suction. If an emulsion exists, a homogeneous phase can be obtained by placing spheres of a molecular sieve in the solution for about 10 minutes. 2 ml of dimethylsulfoxide and quaternary ammonium perchlorate are added to the organic phase obtained in this way, in order to render the medium condutive. The amount of hydrolysis product present is then determined by voltametry. The correlation between the oxidation current and the concentration of the hydrolysis product is given by a calibration curve which has been obtained using a solution which had a composition identical to that of the example.

As can be seen from the text, the invention is not restricted solely by the processes, embodiments and applications described, but also comprises any variants which become obvious to those skilled in the art on reading this description.

We claim:

1. A method for the determination of a protease which comprises reacting said protease with a substrate of the formula A-B, wherein A is N-substituted arginyl or a peptide having a C-terminal arginyl group and B is the residue of an amine electrolytically active amine, B-H, which can be oxidized or reduced electrochemically, whereby said amine is released from said substrate, and the determining the amount of amine which has been released by measuring an electric oxidation or reduction current passed between electrodes immersed in a medium containing said released amine, one of which electrodes is a pre-conditioned measurement electrode.

2. A method as in claim 1 wherein said protease is a blood clotting system protease or a complement protease.

3. A method as in claim 1 wherein said electrodes include said measurement electrode and a reference electrode.

4. A method as in claim 3 wherein said measurment electrode is a noble metal electrode.

5. A method as in claim 3 wherein said measurement electrode is a carbon paste electrode made by mixing carbon powder with a paraffin oil.

6. A method as in claim 1 wherein an auxiliary electrode is additionally present immersed in said medium to ensure the passage of current.

7. A method as in claim 1 wherein said electric oxidation or reduction current is measured at intervals to detect concentration changes for said amine, B-H.

8. A method as in claim 7 wherein said electric oxidation or reduction current is measured by applying a potential having a saw-tooth profile to said electrodes to produce a current/voltage characteristic having a peak value, and determining said peak value.

9. A method as in claim 1 wherein said medium is a heterogeneous medium.

10. A method as in claim 9 wherein said heterogeneous medium is whole blood.

11. A method as in claim 1 wherein said medium is an aqueous medium.

12. A method as in claim 11 wherein said aqueous medium comprises from 2 to 10 percent of dimethylsulfoxide.

13. A method as in claim 1 wherein said medium is a non-aqueous medium.

14. A method as in claim 1 wherein said released amine is isolated prior to determining its amount.

15. A method as in claim 1 wherein said amine B-H is a member selected from the group consisting of aromatic and heterocyclic amines and polyamines.

16. A method as in claim 15 wherein said amine is selected from the group consisting of p-aminodiphenylamine, 4,4'-benzidine, o-anisidine,4-methoxy-2-naphthylamine, and p-nitroaniline.

17. A method as in claim 1 wherein said substrate is activated by the presence therein of an acyl, sulfonyl, tosyl, or benzoyl group.

18. A method as in claim 1 wherein said substrate is benzoyl-arginyl, tosyl-arginyl, tosyl-L-glycyl-L-prolyl-L-arginyl,H-D-phenylalanyl-L-pipecolyl-L-arginyl, N-benzoyl-L-phenylalanyl-L-valyl-L-arginyl, or H-D-phenylalanyl-L-pipecolyl-L-arginyl.

19. A method as in claim 1 wherein said electrolytically active amine is p-amino-diphenylamine and said medium is buffered and has a pH of 8.15.

* * * * *